United States Patent
Perry et al.

(10) Patent No.: US 10,235,646 B2
(45) Date of Patent: Mar. 19, 2019

(54) SYSTEMS AND METHODS FOR AUTOMATED REAL-TIME TASK SCHEDULING AND MANAGEMENT

(71) Applicant: TeleTracking Technologies, Inc., Pittsburgh, PA (US)

(72) Inventors: Thomas Perry, DuBois, PA (US); Steven P. Gaghan, Mars, PA (US); Benjamin Joel Martin, Harmony, PA (US); Raymond C. Lantz, Pensacola, FL (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 14/731,190

(22) Filed: Jun. 4, 2015

(65) Prior Publication Data
US 2016/0300178 A1 Oct. 13, 2016

Related U.S. Application Data

(60) Provisional application No. 62/145,984, filed on Apr. 10, 2015.

(51) Int. Cl.
*G06Q 10/06* (2012.01)
*G06Q 50/22* (2018.01)

(52) U.S. Cl.
CPC ........ *G06Q 10/063112* (2013.01); *G06Q 10/06316* (2013.01); *G06Q 10/063116* (2013.01); *G06Q 50/22* (2013.01)

(58) Field of Classification Search
CPC ....... G06Q 10/03116; G06Q 10/03112; G06Q 10/0316; G06Q 50/22

USPC ................... 705/7.14, 2, 7.26, 7.16
See application file for complete search history.

(56) References Cited

U.S. PATENT DOCUMENTS

| | | | |
|---|---|---|---|
| 7,881,957 B1* | 2/2011 | Cohen | G06Q 10/06 |
| 8,260,736 B1* | 9/2012 | Lear | G06N 5/02 706/46 |
| 2006/0167738 A1* | 7/2006 | Spear | G06Q 10/06 340/573.1 |
| 2007/0100677 A1* | 5/2007 | Boss | G06Q 10/06 705/7.13 |

(Continued)

OTHER PUBLICATIONS

I-Sector Introduces Work Flow Manager Application For Cisco Telephony, FinancialWire (Jul. 2010) (Year: 2010).*

(Continued)

*Primary Examiner* — Charles Guiliano
(74) *Attorney, Agent, or Firm* — Finnegan, Henderson, Farabow, Garrett & Dunner LLP

(57) ABSTRACT

Computer-implemented systems and methods are provided for automated task scheduling and management. In some embodiments, a system for automated task scheduling may comprise at least one processor configured to receive a request with information for a task to be performed by a respondent. The one or more processors may retrieve employee information and, based on one or more attributes in the employee information and one or more attributes in the task information, identify one or more employees to complete the task. The one or more processors may assign the task to the identified employee(s), and monitor a status of the task based on periodic inputs from the employee.

20 Claims, 11 Drawing Sheets

(56) References Cited

U.S. PATENT DOCUMENTS

| | | | | |
|---|---|---|---|---|
| 2008/0164998 A1* | 7/2008 | Scherpbier | ............. | G06Q 10/06 340/539.13 |
| 2012/0173688 A1* | 7/2012 | True | ..................... | G06F 9/4843 709/223 |
| 2013/0275187 A1 | 10/2013 | Patel | | |
| 2014/0278681 A1* | 9/2014 | Cox | ................... | G06Q 30/0641 705/7.19 |

OTHER PUBLICATIONS

The Support Services Suite: System Administration and User's Guide, TeleTracking Technologies, 2006 (229 pages).
ServiceTracking Application: System Administration and User's Guide, TeleTracking Technologies, 2011 (215 pages).
ServiceTracking Application: Web Requester's Guide, TeleTracking Technologies, 2011 (22 pages).
ServiceTracking Application: System Administration and User's Guide, TeleTracking Technologies, 2012 (232 pages).
ServiceTracking Application: Web Requester's Guide, TeleTracking Technologies, 2012 (22 pages).

\* cited by examiner

| | | | | | | | | |
|---|---|---|---|---|---|---|---|---|
| Home | Tasks | Employees | Administration | Placement Request | | | | |

Jobs [          ]

Filter By [All ▽]     Show [25 ▽]     Create Task

28 Results

| Created | Status △ | Task ID | Category | Item | Priority | Req Dept | Origin | Destination |
|---|---|---|---|---|---|---|---|---|
| 4/12 4:02 PM | Pending | 150412 | Insert | (1) Central Line | Medium | CPM | 4000-B | -- |
| 4/12 3:54 PM | Pending | 150411 | Consult | -- | Medium | BNM | 4001-A | -- |
| 4/13 2:14 PM | Assigned | 150428 | Deliver | (1) Bariatic Bed | Medium | QA | 4000-B | -- |
| 4/13 2:51 PM | Assigned | 150422 | Clean | (2) Infusion Pump | Medium | mci | Nurses Station | -- |
| 4/15 10:22 AM | Assigned | 150421 | Insert | (1) Infusion Pump | Medium | -- | Nurses Station | -- |
| 4/14 5:16 PM | Assigned | 150418 | Deliver | -- | Medium | -- | 4000-B | -- |
| 4/13 6:32 PM | Assigned | 150416 | Clean | -- | High | HERE | Booth | -- |

Show [25 ▽]     Prev [1 ▽] of 2 Next

28 Results

Employees

| | |
|---|---|
| Allan Kawakami | Available Complete 0 of 0 |
| Allan Kawakami | Available Complete 0 of 0 |
| Thomas Petty | Dispatched Complete 0 of 4 |
| Sam Adams | Dispatched Complete 0 of 0 |
| Joshua Wenzel | Logged Out Complete 0 of 0 |
| Paul Gagnon | Logged Out Complete 0 of 1 |
| Mark Holoska | Logged Out Complete 0 of 0 |
| John Smith | Logged Out Complete 0 of 0 |
| Sarah Smith | Logged Out |

SYSTEMS AND METHODS FOR AUTOMATED REAL-TIME TASK SCHEDULING AND MANAGEMENT

PRIORITY CLAIM

This application claims priority from U.S. Provisional Application No. 62/145,984, filed Apr. 10, 2015, which is hereby incorporated by reference in its entirety in the present application.

BACKGROUND

Modern hospitals treat hundreds of patients every day. In addition to the doctors and nurses caring for patients, there are many departments and teams of support staff that support the infrastructure of the hospital assigned to ensure that rooms are clean, equipment is sanitized and in working condition, and that people and items are moved to the right place at the right time. Orchestrating the activities of distinct departments in a hospital is a tremendous feat of organization and communication, and inefficiencies often result from miscommunication and insufficient task tracking.

Current systems rely on dispatchers to receive manually-generated task requests and send employees to complete the task, and often times both the dispatcher and the requester do not know if or when the task was completed, or whether a qualified employee completed the task. This results in delayed care, less direct patient care, poor patient outcomes and dissatisfaction, redundant communications, poor visibility into service request progress, long wait times/unfinished requests, among other problems. In view of the deficiencies of current systems, improved systems and methods for performing automatic real-time task scheduling and tracking are desired.

SUMMARY

Disclosed embodiments relate to automatically assigning and managing tasks. Disclosed embodiments may provide for consistent responses to requests for one or more tasks, allowing for automated workflow for support in a facility such as a medical facility, hotel, or any other type of facility that benefits from support and maintenance teams. As discussed below, the disclosed embodiments may improve response time, streamline communications between departments in a facility, and provide for intelligent task assignment and dispatching based on multiple factors such as proximity, skill set, workload, and task priority.

Consistent with the present embodiments, a system is disclosed. The system may include at least one processor and a storage medium. The at least one processor may be configured to execute instructions stored in the memory to automatically assign a task. The processor may be configured to execute the instructions to receive, at the at least one processor from a network, task information for a task that is pending assignment, the task information including a task start time, at least one task location, and one or more required skills; receive, from a networked database, first employee information associated with a first employee, the first employee information including at least one employee skill and at least one employee location; compare the task information and the first employee information; determine, based on the comparison, one or more matches among the task location and the at least one employee location, and between the one or more required skills and the at least one employee skill; assign the task to the first employee based on the one or more determined matches; and create a database entry reflecting the assigned task.

Consistent with the present embodiments, a method for automatically assigning a task is disclosed. The method may comprise receiving, by at least one processor from a network, task information for a task that is pending assignment, the task information including a task start time, at least one task location, and one or more required skills; receiving, from a networked database, first employee information associated with a first employee, the first employee information including at least one employee skill and at least one employee location; comparing the task information and the first employee information; determining, based on the comparison, one or more matches among the task location and the at least one employee location, and between the one or more required skills and the at least one employee skill; assigning the task to the first employee based on the one or more determined matches; and creating a database entry reflecting the assigned task.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIG. 8 is an illustration of an example of a task creation interface, consistent with embodiments of the present disclosure;

FIG. 9 is an illustration of an example of a task assignment interface, consistent with embodiments of the present disclosure;

DETAILED DESCRIPTION OF EXEMPLARY EMBODIMENTS

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
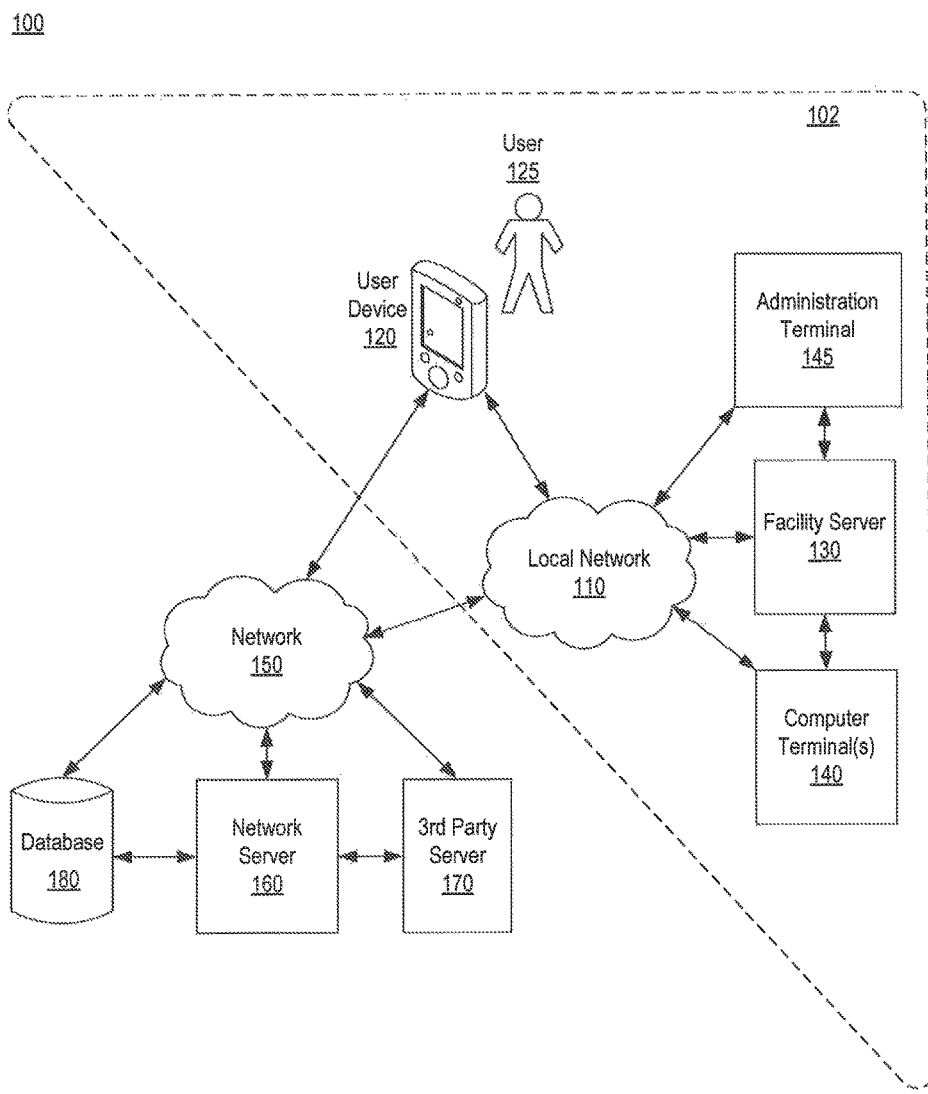
FIG. 1 depicts an example of a system environment for scheduling and managing tasks within an organization, consistent with embodiments of the present disclosure.

FIG. 1 shows a diagram of a workflow automation and management system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, workflow automation and management system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a hospital or office building (i.e. as facility system 102) while network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include computer system or device associated with a user 125 that manages or oversees a portion of facility system 102. For example, administrator terminal 145 may comprise a computer system located at a head nurse station, a housekeeping manager's office, or any other department manager's office or station.

User 125 may be an employee in a workplace environment such as a nurse, a technician, or a dispatcher. User 125 may operate computer terminal 140, user device 120, and/or another computer (not shown) to interact with system 100. System 100 may include multiple types of users such as, for example, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital, business, retail location, and the like. Facility server 130 may enable communication within a computer-based system including computer system components such as desktop compute workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, Third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
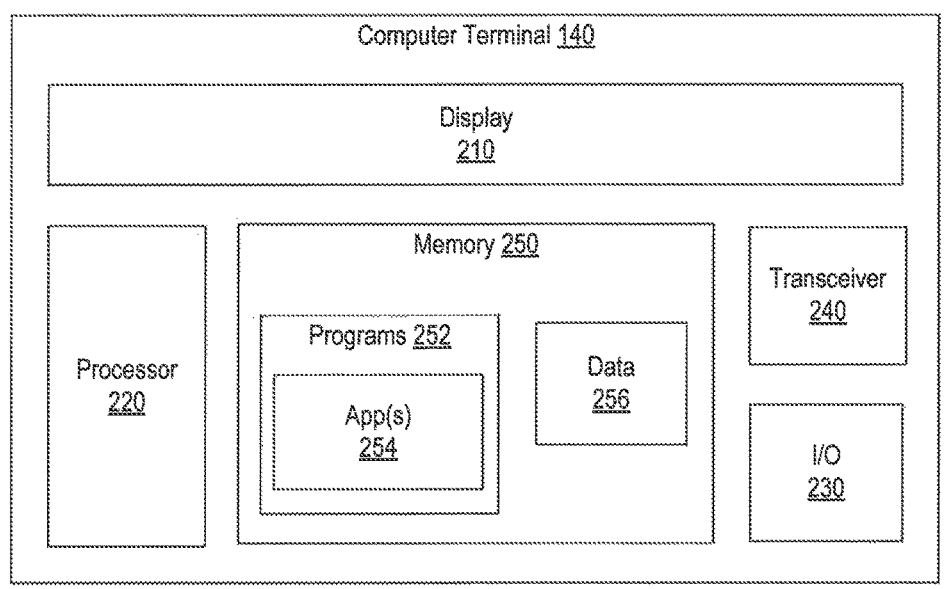
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens Processor 220 may be one or more known processing devices, such as a microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for prioritizing and assigning tasks to one or more employees.

Program(s) 252 may include operating systems (not shown) that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a task administration app, which when executed causes computer terminal 140 to perform processes related to managing, prioritizing, and scheduling multiple pending tasks. For example, app(s) 254 may configure computer terminal 140 to perform operations including receiving input of task information, displaying pending tasks, monitoring task status, assigning tasks to employees, and displaying employee task assignments.

Figure 3:
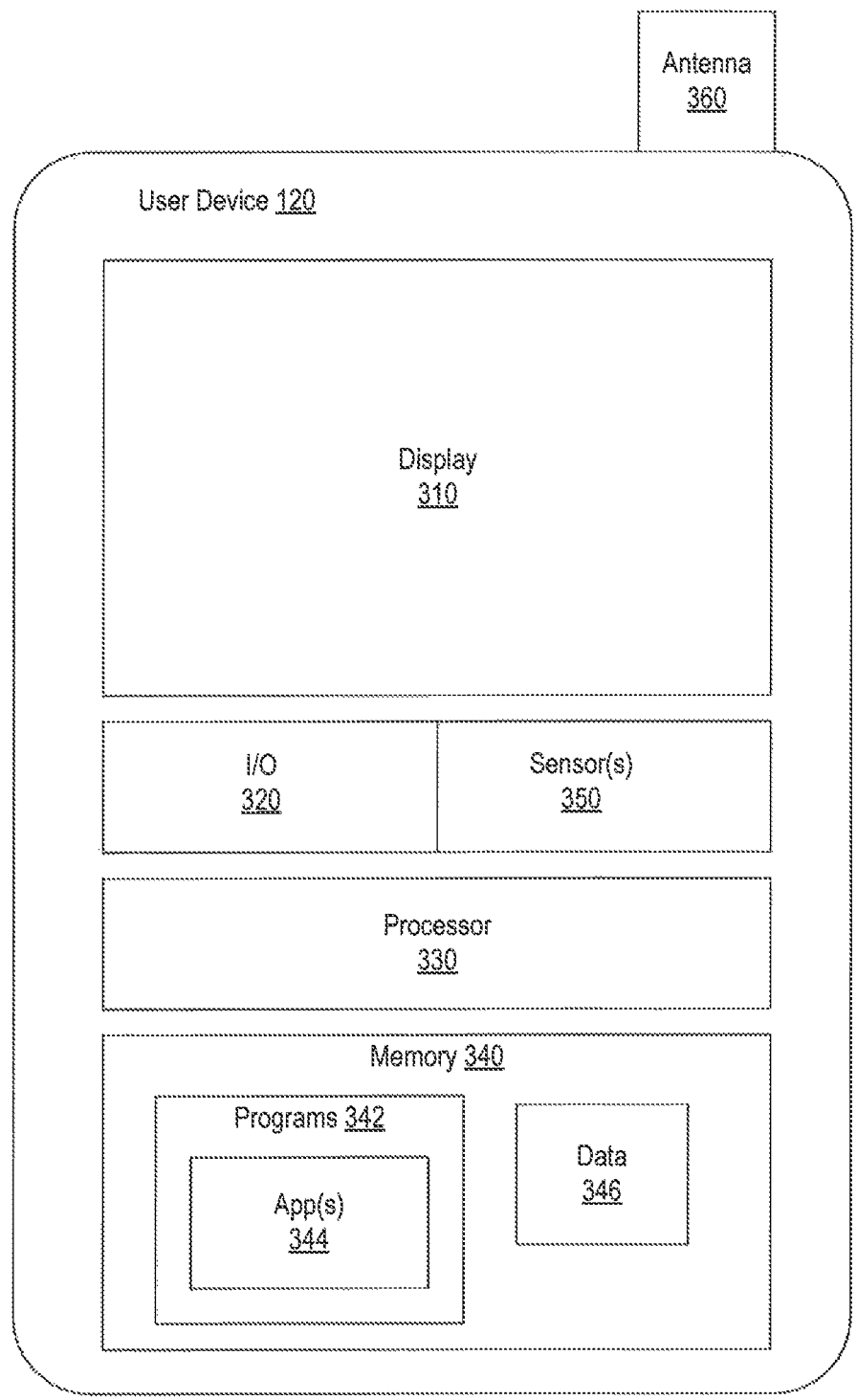
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
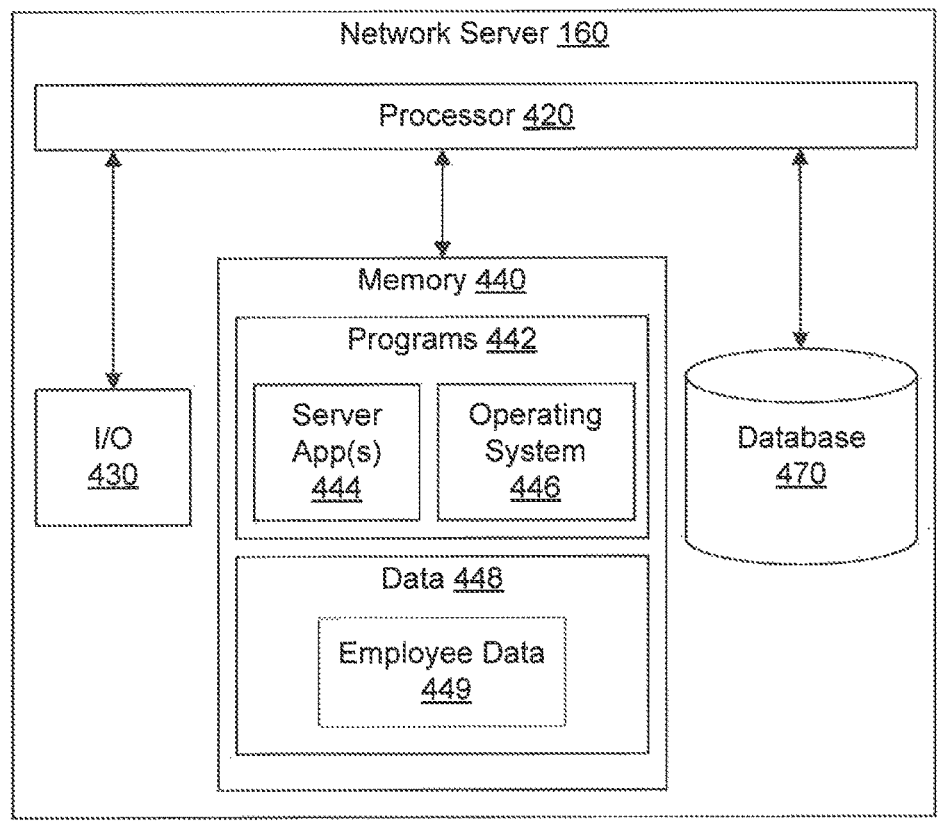
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure or Amazon Web Services. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as a request for an equipment item to be transported between facilities. Additionally, network server 160 may collect data from multiple facilities to evaluate performance times in different facilities, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448, and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of task information, display pending tasks, monitor task status, assign tasks to employees, and display employee task assignments In some embodiments, memory 440 may store data 448 including data associated with employees, tasks, assets, assignment algorithms, and any other data related to the disclosed embodiments. For example, data 448 may include one or more entries including identifications of employees, their skill sets, their schedules and availability, employee locations (expected locations/posts, and real-time locations), and tasks assigned to each employee. Data 448 may also include one or more entries including attributes related to previous tasks and pending tasks, such as task priority levels, task durations, task origin and destination locations, asset items associated with tasks, asset locations associated with tasks, employee information for employees that previously performed particular tasks, and any other data related to task attributes, task requirements, and task performance. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
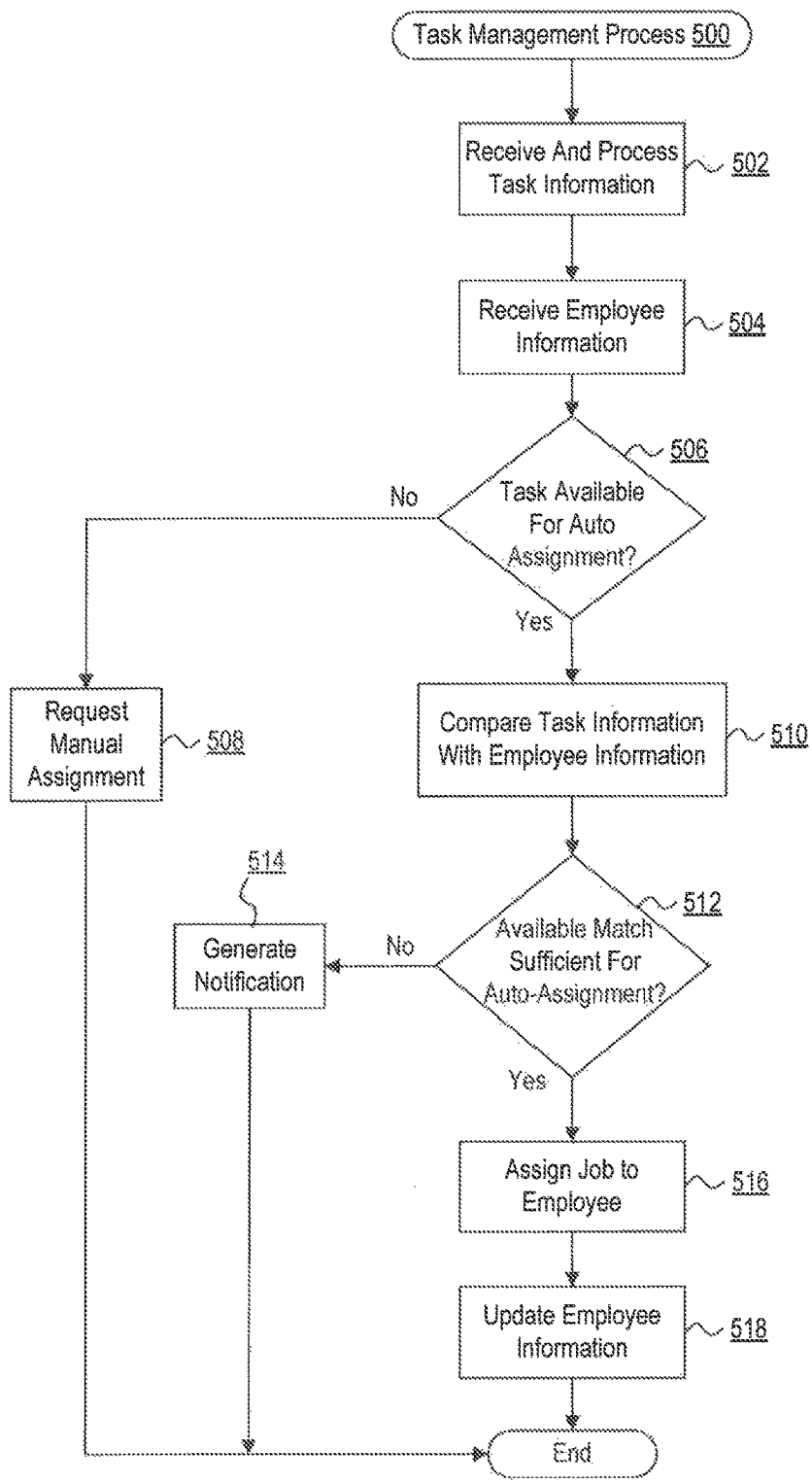
FIG. 5 is a flowchart of an example of a process for automated task scheduling and management, consistent with embodiments of the present disclosure.

FIG. 5 shows a flowchart of an exemplary task management process 500. Process 500 is described herein as performed primarily by network server 160, however in some embodiments, facility server 130, computer terminal 140, administration terminal 145, user device 120, and/or third party server 170 may perform one or more steps of process 500.

Process 500 may begin in step 502 when network server 160 receives and processes task information for a new task request. In some embodiments, network server 160 may receive a task request from a terminal such as computer terminal 145, administration terminal 145, and/or user device 120. In some embodiments, task requests may include a text message, email, communication from app 254 or 344, or other written request from any electronic device in communication with network server 160. In some embodiments, network server 160 may receive one or more task requests via another interface, such as an interactive voice response (IVR) system, or touch-tone phone entry system. Network server 502 may process the received task information to extract one or more attributes about the task. In some embodiments, network server 502 may determine whether multiple pending requests are associated with a similar location, task, and/or equipment or supplies.

In such embodiments, network server 160 may determine whether multiple similar tasks may be grouped together into a batch, to be performed by a single employee (not shown in figures). In some embodiments, network server 160 may even determine whether a task that is already assigned to another employee is in progress and, if not, network server 160 may unassign the task dynamically and include the unassigned task in a batch of tasks for a single employee. Thus, network server 160 may identify an efficient manner for completing pending tasks using fewer employees, when appropriate.

In step 504, network server 160 may receive employee information, such as employee data 449 retrieved from any of memory 440. In some embodiments, network server 160 may determine which employees are currently available based on, for example, one or more work schedules or computer entries indicating that the employee is presently at the facility and working. Network server 160 request and receive employee information for the employees that are available at the time of the task request.

In some embodiments, network server 160 may retrieve employee information from database 180, or from any other memory associated with components of system 100. In some embodiments, employee information may include one or more attributes associated with the employees of the facility. For example, employee information may include a job title, certifications, qualifications, skill sets, dates and times scheduled to work, expected location of work, expected current location, detected current location, tasks currently assigned to the employee, a status of the assigned tasks, and performance data related to previous tasks.

In some embodiments, employee location may include a room, department, or area of a facility assigned to the employee in a work schedule, a manual entry from the employee, a detected location based on locating equipment, or any other means of designating an employee's location within a facility. In some embodiments, employee location may include coordinates such as latitude and longitude, distance from particular landmark in the facility, or one or more designations of locations in the facility, such as buildings, floors, units, zones and/or room numbers. Employee location may include both a designation of a specific location and one or more designations of more general location (e.g., room and zone).

In some embodiments, employee information may include a history of tasks that the employee has performed, and one or more statistics associated with the employee's performance of the tasks. For example, employee information may include information identifying completed tasks, date and time of task assignment (start time) and completion (end time), and other historical information regarding past tasks.

In step 506, network server 160 may determine if the requested task is eligible for automatic assignment to one or more employees. For example, network server 160 may determine whether the requested task is associated with one or more predetermined categories of tasks that are eligible for automatic assignment. In some embodiments, network server 160 may store categories of tasks that are suitable for automatic assignment, and task categories that are unavailable for automatic assignment due to safety considerations, or task categories that include factors not yet integrated into the rule sets integrated within network server 160.

If the task is ineligible for automatic assignment ("no" in step 506), process 500 may proceed to step 508, in which network server 160 generates a notification to request manual assignment of the task. In some embodiments, the generated notification may appear as an alert on one or more of user device 120, computer terminal 140, and/or administration terminal 145. For example, in some embodiments, network server 160 may send an email or text message to an appropriate user 125, to request manual assignment of the new task. Upon receiving a manual assignment of the new task, process 500 may end. In some embodiments, network server 160 may create and/or update one or more database entries for employee information and task information, to reflect the manual task assignment.

If network server 160 determines that the new task is available for automatic assignment ("yes" in step 506), then in step 510 network server 160 may compare task information for the requested task to received employee information. Step 510 is described in further detail with respect to FIG. 6.

In step 512, network server 160 may determine whether at least one employee matches the requested task, and whether the results of step 510 include one or more matches suitable for auto-assignment. In some embodiments, network server 160 may evaluate one or more matches produced in step 510. If no matches are suitable for auto-assignment ("no" in step 512), in step 514 network server 160 may generate one or more notifications that an automatic assignment was not possible, based on the received task information and available employees. Similar to step 508, the notifications may appear as an alert on one or more component of system 100, such as user device 120, computer terminal 140, or administration terminal 145. In some embodiments, network server 160 may generate an email or text message to an individual and/or device outside of facility system 102 (not shown in figures).

If network server 160 identifies at least one suitable employee match for auto-assignment to the task ("yes" in step 512), then in step 516 network server 160 may assign the task to one or more employees. Step 516 is described in further detail with respect to FIG. 7.

In step 518, network server 160 may update employee information to reflect the task assignment. In some embodiments, network server 160 may create and/or update one or more database entries with the updated employee information immediately, or nearly immediately. In some embodiments, network server 160 may also generate one or more alerts to notify one or more employees of the updated employee information, via one or more components of system 100. For example, network server 160 may generate an alert notifying a responder employee that that a new task is assigned to them. In some embodiments, network server 160 may generate one or more alerts to requester employee(s), to inform the requester(s) that the task is assigned to a responder employee. Network server 160 may send such notifications to user device 120, administration terminal 145, and/or computer terminal 140.

In some embodiments, network server 160 may create and/or update one or more database entries including task information for the newly assigned task (not shown in figure). For example, network server 160 may store a database entry identifying the task, a request time, an assignment time, an employee identification of the requestor(s), an employee identification of the dispatcher (if any), an employee identification of the responder(s), an origin location of the task, a destination location of the task, any assets, equipment, food, medicine, or other supplies associated with the task, an expected completion time, and any custom comments associated with the task received from one or more of the requester, dispatcher, and respondent. In some embodiments, stored employee and task database entries may be accessible to users 125 including requestors, dispatchers, and responders via one or more of mobile device 120, computer terminal 140, and/or administration terminal 145.

Figure 6:
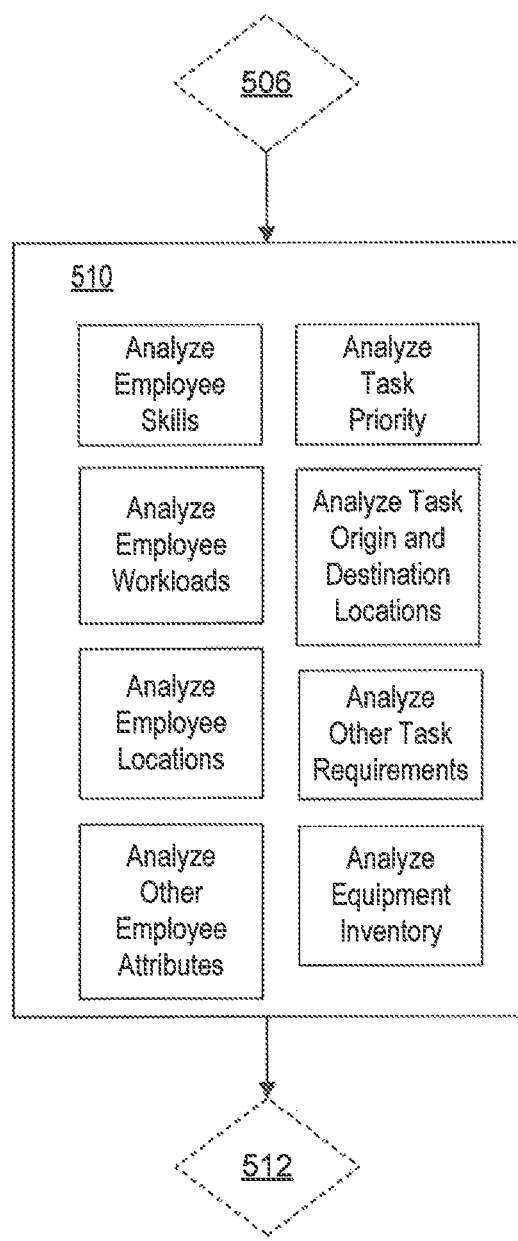
FIG. 6 is a flowchart of an example of a process for comparing task information and employee information, consistent with embodiments of the present disclosure.

FIG. 6 is a flowchart of an example of a process for comparing task information and employee information 510. As shown in FIG. 6, network server 160 may analyze a plurality of factors during step 510, to identify one or more matches between employees and the task information. Network server 160 may perform one or more analyses of step 510 in parallel or in varying sequences, depending on the needs of the requestor, dispatcher, or the facility. In some embodiments, network server 160 may score the results of each analysis, to generate a numerical score that may be used to rank available employees for selection. In some embodiments, each analysis may be weighted, depending on the priorities and needs of the facility, of a requester or dispatcher, or of a facility administrator. Step 510 may also include more or fewer analyses depending on the types of available employee information, and attributes included in the task information.

In some embodiments, network server 160 may analyze employee skills. For example, network server 160 may determine the skill sets and/or certifications associated with each available employee. Skill sets and certifications may include indications entered manually by the employee's supervisor, trainer, or other authority figure. In some embodiments, network server 160 may automatically store skill sets and/or certifications in association with employees, based on previously completed tasks.

In some embodiments, network server 160 may compare employee skills and certifications to one or more task requirements. For example, network server 160 may determine whether a requested task requires any particular skill sets and/or certifications, and filter the available employees based on this determination. In some embodiments, network server 160 may rank available employees based on a quantity of relevant skill sets and/or certifications, so that the most qualified employees for the task are prioritized over lesser-qualified employees.

In some embodiments, network server 160 may analyze employee workloads. For example, network server 160 may determine how many tasks are currently assigned to each employee, compared to a total number of tasks that may be assigned to the employee at any given time. In some embodiments, a total number of tasks may include a manual database entry from an administrator or supervisor. In other embodiments, network server 160 may automatically and dynamically determine a total number of tasks that can be assigned to the employee at any given time, based on prior performance statistics and workloads. For example, if network server 160 determines that employee A previously handled 4 tasks simultaneously in a timely manner without any problems, network server 160 may automatically increase employee A's total number of tasks to 5 tasks. In some embodiments, network server 160 may rank available employees according to a number or percentage of available task slots, so that employees with fewer currently assigned tasks are prioritized for assignment over employees who have full or nearly-full current workloads.

In some embodiments, network server 160 may analyze employee locations. For example, network server 160 may determine an expected location for each employee, based on the employee's job title, job assignment, work schedule, or other database entry identifying an expected location for the employee. In some embodiments, employees may wear one or more electronic tags that can transmit a location signal to network server 160. In such embodiments, network server 160 can maintain a database of each available employee's real-time location in the facility. In some embodiments, user device 120 may include one or more location sensors, and user device 120 may transmit a real-time location signal to server 160, to provide a current location of an employee associated with the user device 120.

In some embodiments, network server 160 may compare employee locations to one or more locations associated with a requested task, such as the task origin location, task destination location, and one or more locations of equipment and supplies associated with the requested task. As an example, network server 160 may determine which employees are currently located, or are expected to be located, closest to a location whether the requested task originates. For example, if a requested task involves moving a bariatric hospital bed from supply room A to patient room 100, network server 160 may determine which available employees are currently located in closest proximity to supply room A, where the moving task originates. As another example, if the requested task indicates that a second employee is required to set up the bariatric bed in patient room 100 (but that only a single employee is needed to move the bed to patient room 100), then network server 160 may identify one or more available employees currently located closest to the task destination location (patient room A), to assign as the second employee for the task. In some embodiments, network server 160 may rank available employees based on proximity to the origin and/or destination locations for the task.

In some embodiments, network server 160 may analyze other employee attributes and other task requirements. For example, network server 160 may determine whether any available employees have restrictions or disabilities that may prevent them from being able to perform the requested task. Additionally, network server 160 may determine whether employees are scheduled to be on a break, or are located in a location of the facility associated with a break period, lunch period, or other location that may affect the employee's availability status for the task.

In some embodiments, network server 160 may analyze a priority of the requested task. In some embodiments, task priority may be indicated manually by the requestor and/or dispatcher when the task request is created. In other embodiments, network server 160 may assign a priority level to the task based on one or more stored rule sets that may take into account factors such as, a requested time frame for completing the task, the nature or type of task, a location of the task (such as an emergency room or operating room), and any other factors related to an indication or urgency or importance. In some embodiments, network server 160 may attempt to assign high priority tasks to employees associated with more skills and certifications, employees who do not currently have any assigned tasks and can begin a high priority task immediately, or employees who have historically handled high priority tasks within a predetermined time frame and without errors.

In some embodiments, network server 160 may analyze one or more attributes regarding assets associated with the requested task such as equipment and/or supplies. For example, network server 160 may determine an inventory level of required equipment and/or supplies, a location of the equipment and/or supplies, instructions associated with the equipment and/or supplies, and required certifications or skills associated with the equipment and/or supplies. In some embodiments, network server 160 may determine a location of the assets based on one or more database entries indicating an expected location (such as a supply room) of the assets. In other embodiments, assets may be tagged with one or more electronic devices for broadcasting a location, condition, and inventory level of certain assets, and network server 160 may determine a real-time location, inventory level, and condition of each tagged asset. In some embodiments, network server 160 may compare the attributes to employee attributes such as, for example, employee location, employee skill sets and certifications, prior experience with certain equipment and/or supplies, and any other attributes related to the equipment and/or supplies, in order to identify one or more employees that match the equipment attributes. In some embodiments, network server 160 may rank or score the available employees based on a quantity or amount of matching or compatible attributes between the employee attributes and equipment attributes.

At the completion of step 510, network server 160 may create a ranked list of available employees based on one or more scores and/or rankings of individual analyses. In some embodiments, network server 160 may assign a weighting to one or more of the scores and/or ratings for each analysis, based on the needs of the requestor, dispatcher, and/or the facility. In some embodiments, weightings for different analyses may be stored as a rule set and accessed by network server 160 during step 510.

Figure 7:
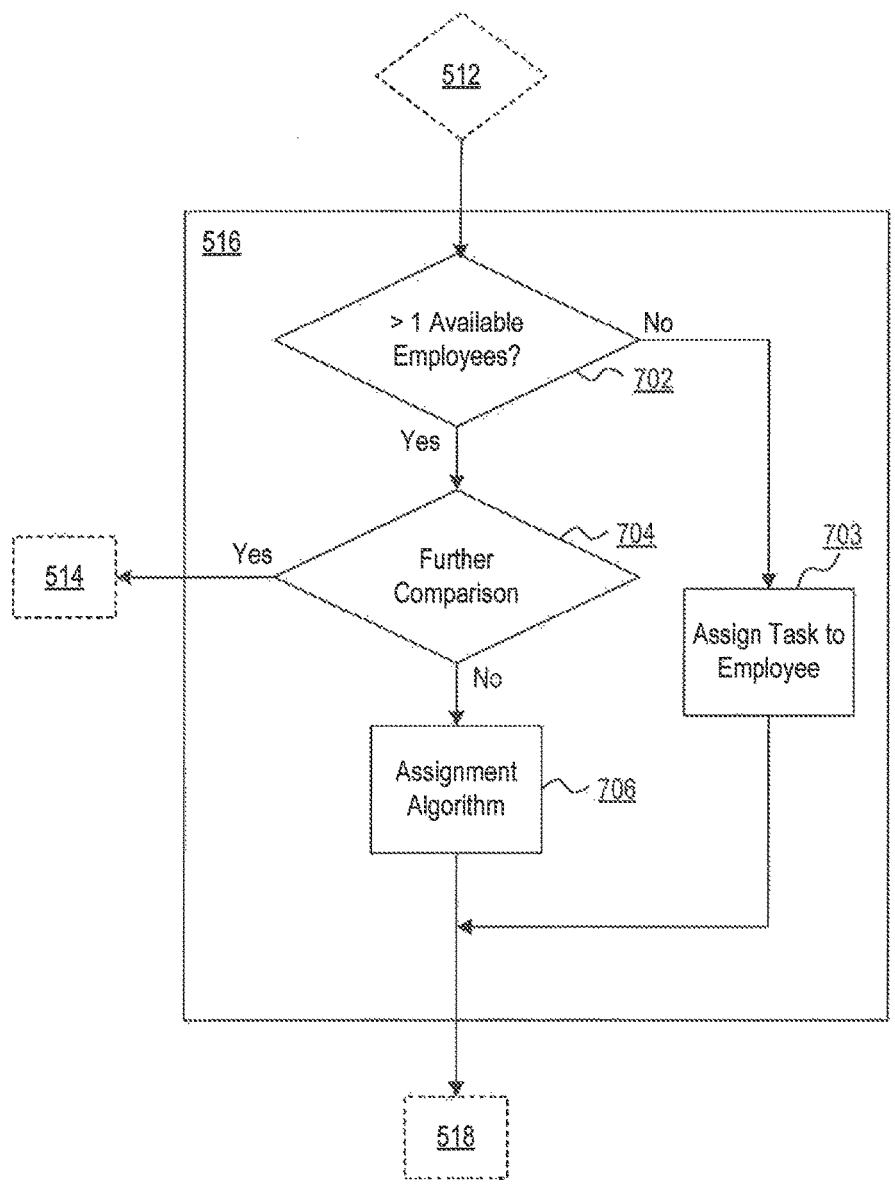
FIG. 7 is a flowchart of an example of a process for assigning a task to an employee, consistent with embodiments of the present disclosure.

FIG. 7 is a flowchart of an example process for identifying an available match sufficient for auto-assignment 512 that may take place as a part of process 500. As shown, in step 702, network server 160 may determine whether there is more than 1 employee identified in step 510 that matches task requirements and attributes. If only one employee is identified ("no" in step 702), then in step 703 network server 160 may automatically assign the task to the single identified employee. Network server 160 may then proceed to step 518 (of process 500, shown in FIG. 5). If more than 1 employee was identified in step 510 ("yes" in step 702), then in step 704 network server 160 may determine whether further comparison is required before assigning an employee to the requested task. For example, if multiple employees are ranked and/or scored equally (an example determination of "yes" in step 704), then process 500 may proceed to step 514 in which network server 160 may generate one or more notifications and request input from a dispatcher for assigning the task. In some embodiments, network server 160 may determine whether further comparison can be conducted to further narrow the number of potential employees for assignment of the task. For example, while one or more attributes may be sufficient for a match if only one employee is available with those attributes, a more optimized match may be sought if additional employees are available. In such embodiments, step 510 may apply a first set of filters and rules to narrow down a pool of potential employees, and in step 704 network server 160 may determine whether a second set of filters and/or rules should be applied to the remaining pool of potential employees, to identify a highly targeted list of employees. In some embodiments, in step 704 network server 160 may determine whether a threshold number of potential employees is exceeded, indicating a need for additional comparison. If further comparison is to be applied ("yes" in step 704), process 500 may return to step 510 (not illustrated in FIG. 7).

If network server 160 determines that further comparison is not required, then in step 706 network server 160 may apply one or more assignment algorithms for assigning the requested task to one or more employees. In some embodiments, network server 160 may implement a round-robin type of assignment algorithm, in which network server 160 cycles through a pre-ordered list of available employees that match the task requirements and attributes, and network server 160 may continue assigning tasks to the next employee listed, until the employee's workload capacity is reached (e.g., the total number of task slots for a particular employee are filled). In some embodiments, network server 160 may identify a highest ranked or highest scored employee, based on the results of step 510, and attempt to assign the task to that employee. If the employee becomes unavailable or refuses to accept the task, then network server 160 may assign the task to the next-highest ranked/scored employee, until the task is accepted and started. In other embodiments, network server 160 may employ one or more other assignment algorithms for assigning tasks to employees that take into account an employee availability, employee workload and skill set, and attributes of the requested task. After assigning the task, process 500 may proceed to step 518 (shown in FIG. 5).

In some embodiments, network server 160 may reevaluate existing task assignments to promote an even distribution of work among active employees. Network server 160 may be configured to periodically evaluate workload disparities among employees and, if necessary, automatically reassign tasks to reduce such disparities. For example, network server 160 may compare the number of tasks assigned to an employee to the number of tasks assigned to other employees, or to an average number of tasks currently assigned to active employees. If the difference is greater than a predetermined threshold, network server 160 may use process 500 to automatically reassign tasks, reducing the difference.

Other means of quantifying workload, such as expected time to complete the task, may be used to determine whether tasks should be reassigned. Automatic task reassignment may occur on a real-time, ongoing basis, on a schedule, periodically (e.g., every hour), or based on the occurrence of predetermined events which could indicate a disparity or potential disparity in workload. Such events could include, for example, an employee becoming active or inactive or a particular number of manual task assignments being received within a given period of time.

FIG. 8 is an illustration of an example of a task management interface 800, consistent with disclosed embodiments. Task management interface 800 may be displayed, for example, at computer terminal 140 or administrator terminal 145 based on communication over local network 110 and/or network 150. An administrator or other employee responsible for overseeing task management may interact with administrator terminal 145 in order to operate task management interface 800. Task management interface 800 may include a list of tasks active in system 100, and employee list 806 that includes a number of assigned and completed tasks associated with each employee. In some embodiments, employee list 806 may indicate one or more statuses for each employee such as, for example, whether an employee is "available" (e.g., on duty and not working on any task), "dispatched" (e.g., on duty and currently working on a task), or "logged out" (e.g., off duty). In some embodiments, employee list 806 may display more or fewer statuses depending on the types of data collected and the needs of the facility and its administrators. In other embodiments, employee list 806 may indicate a number of tasks that a particular employee has completed, out of the total number of tasks assigned during the employee's time on duty.

In some embodiments, the list of tasks in task management interface 800 may be organized based on task attributes 802, such as creation date and time, progress status, task identification number, task category, associated assets such as equipment and/or supplies, task priority, associated departments, origin location and/or destination location associated with the task. Other attributes that may be associated with a task will be apparent to those of skill in the art.

In some embodiments, task management interlace 800 may provide a real-time status of each pending task in the facility, or a particular department of the facility. For example, when the facility is a medical facility, task management interlace 800 may display all tasks for a particular department such as maintenance, housekeeping, food service, medical equipment delivery, medical transport, and any other support departments or teams within the medical facility. In some embodiments, one or more administrative terminals 145 may display a task management interface 800 that displays all tasks for the entire medical facility.

In some embodiments, task management interface 800 may provide a real-time status for each task based on continuously collected data from one or more of user device 120, computer terminal 140, administrative terminal 145, one or more tracking devices such as real time locating system (RTLS) tags, one or more sensors located throughout the facility such as proximity sensors, temperature sensors, presence sensors, door and room access sensors, and manual inputs via IVR or other manual entry systems. In some embodiments, network server 160 may receive real-time data streams associated with the status of a task, including indications from users 125 via user device 120 that a task is started, completed, delayed, or that a milestone of the task is completed. In some embodiments, network server 160 may track a duration of each task in progress, and determine an expected completion time for each task based on a plurality of factors such as, for example, an average historical time to complete a similar type of task, the assigned employee's current workload and historical timeliness rating, indications of potential or confirmed delays based on input from the assigned employee, and any other factors relevant to an expected duration and/or completion time of the task. In some embodiments, task management interface 800 may display an expected completion time for each task, elapsed duration for each task, and expected or confirmed length of delay for each task.

In some embodiments, task management interface 800 may provide, upon request via interface 800, additional details for particular tasks including, for example, details for completion or progress of each step of the task since the task began up to the current time (real-time). In some embodiments, interface 800 may provide or more configurable alerts to the task requester and/or dispatcher, if the employee does not complete the task within a predetermined period of time, or if the employee is determined to be in a location of the facility that is inconsistent with the pending assigned task.

In some embodiments, an additional window or popup window (not shown in figures) may appear displaying details for a particular task including a creation time, a time of assignment, a time that the assigned employee began the task, a time of reassignment (if any), times and durations of delays, a completion time of task steps, and any other milestones that are associated with one or more timestamps that can be In some embodiments, task management interface 800 may include a button for creating a new task, such as interface element 804. Upon receiving a selection of interface element 804, network server 160 may generate information for displaying task creation interface 900, as illustrated in FIG. 9.

Figure 9:
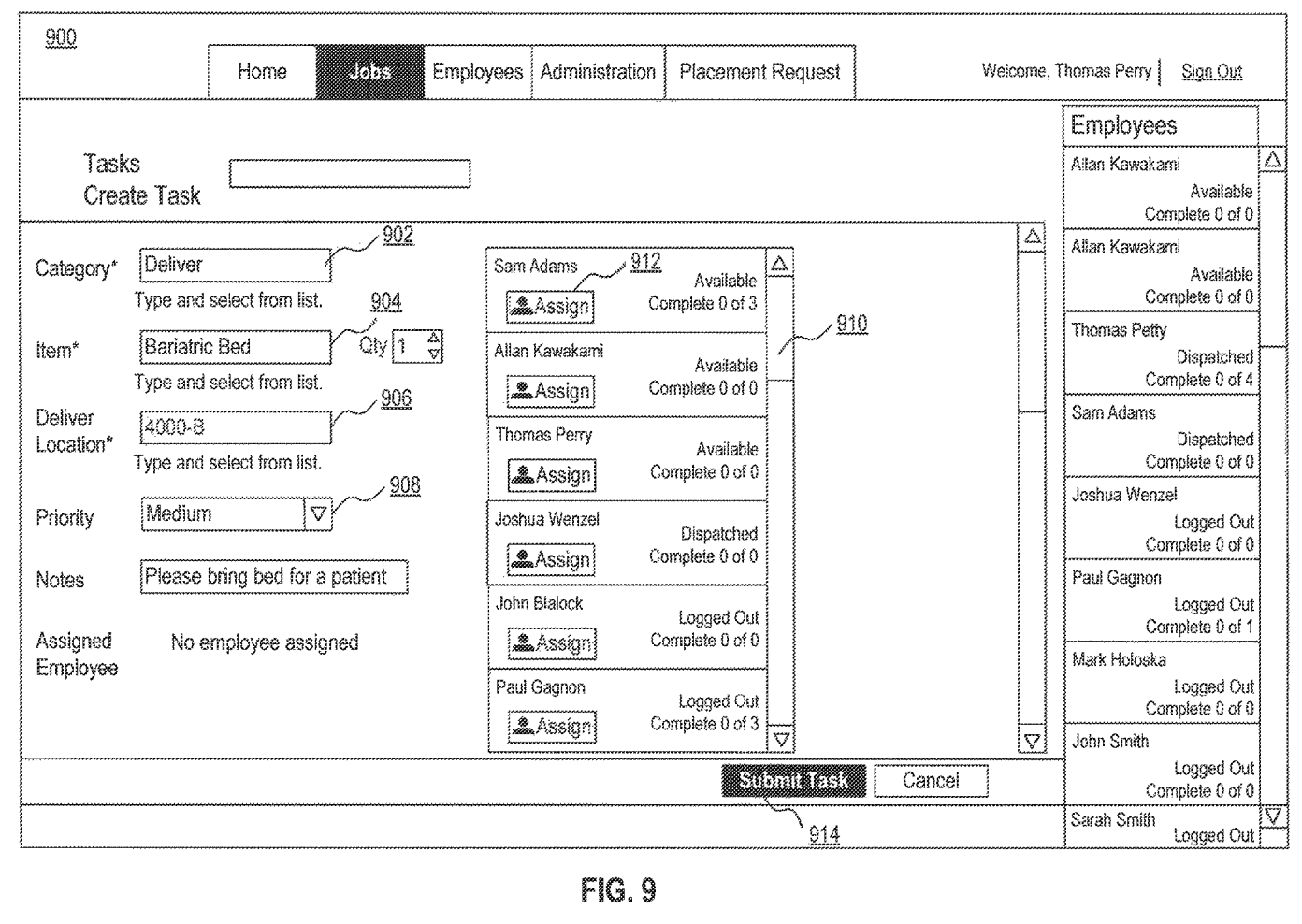

FIG. 9 is an illustration of a task creation interface 900, consistent with disclosed embodiments. Task creation interface 900 may allow a user 125 (such as a requestor and/or dispatcher) to create a customized task request with specific instructions for the responder. In some embodiments, interface 900 may include options for specifying the full details of the task such as, for example, the type of task, origin location, destination location, and equipment and/or supplies associated with the task. In some embodiments, network server 160 may access one or more database entries that associate predetermined tasks with one or more of origin and destination locations, equipment and/or supplies, equipment and/or supply locations, equipment and/or supply quantities, priority levels, required skills and/or certifications, and any other attributes which can be stored in association with one or more tasks. In such embodiments, a requestor or dispatcher may only need to identify the task requested, a task location, a desired start time, and/or a desired completion time. Thus, network server 160 may automate significant aspects of the process for requesting a task and assigning the task, streamlining communication, management, workload distribution, and efficiency in the facility. In a facility such as a hospital, such improvements may significantly increase quality of care by shortening response times and increasing an amount of time and effort that caregivers can provide to patients rather than generating requests, following-up on requests, and handling other aspects of task requests that are usually delegated to respondents.

In some embodiments, task creation interface 900 may include one or more detail fields 902, 904, 906, and 908 to allow a requester or dispatcher to specify one or more attributes associated with a new task, such as attributes 802 of FIG. 8. In some embodiments, one or more of details fields 902, 904, 906, or 908 may populate automatically based on selections for one or more of the other fields. For example, interface 900 may include field 902 for entry of a task category. Interface 900 may also include field 904 for entry of an item, such as a piece of equipment, associated with the task. Interface 900 may also include field 906 for entry of a location associated with the task. In some embodiments, interface 900 may include field 908 for entry of a priority associated with the task.

Embodiments consistent with the current disclosure may include additional or alternative fields as a part of interface 900. Furthermore, one or more fields included in new task interface 900 may be generated sequentially or dynamically as information is entered, such that additional fields may be displayed based on entries in previously displayed fields. In some embodiments, network server 160 may automatically populate one or more of fields 904, 906, or 908 based on a task category selected in field 902. For example, if a requester selects "infusion pump delivery" for field 902, network server 160 may automatically determine where infusion pumps are stored, an inventory and maintenance condition of the stored infusion pumps, and automatically populate a field indicating the infusion pump location. Network server 160 may automatically select another infusion pump storage location once the requestor identifies the destination location for the infusion pump, to select a storage location that is closest to the destination location. Upon creating the new task, network server 160 may determine which employee(s) are available that are located closest to the infusion pump storage location, are qualified to handle infusion pumps, and have at least one task slot available to deliver the infusion pump by the requested time or within an average expected delivery time.

In some embodiments, interface 900 may include list 910 displaying potential employees for assignment of the new task. List 910 may include all employees, employees available for assignment of a new task, or only those employees which meet criteria identified in task attribute entry fields. In some embodiments, the employees and/or ranking of employees in list 910 may change dynamically in response to each field input. In some embodiments, list 910 may include a button for manually assigning one or more employees to a new task, such as interface element 912, in association with one or more of the employees in list 910. In response to a selection of one or more interface elements 912, network server 160 may assign the new task to the employee associated with the selected interface element 912.

In some embodiments, new task interface 900 may include a button for submitting the new task, such as interface element 914. Upon receiving a selection of interface element 914, network server 160 may finalize entry of the new task and execute process 500 to assign the task to one or more employees.

Figure 10:
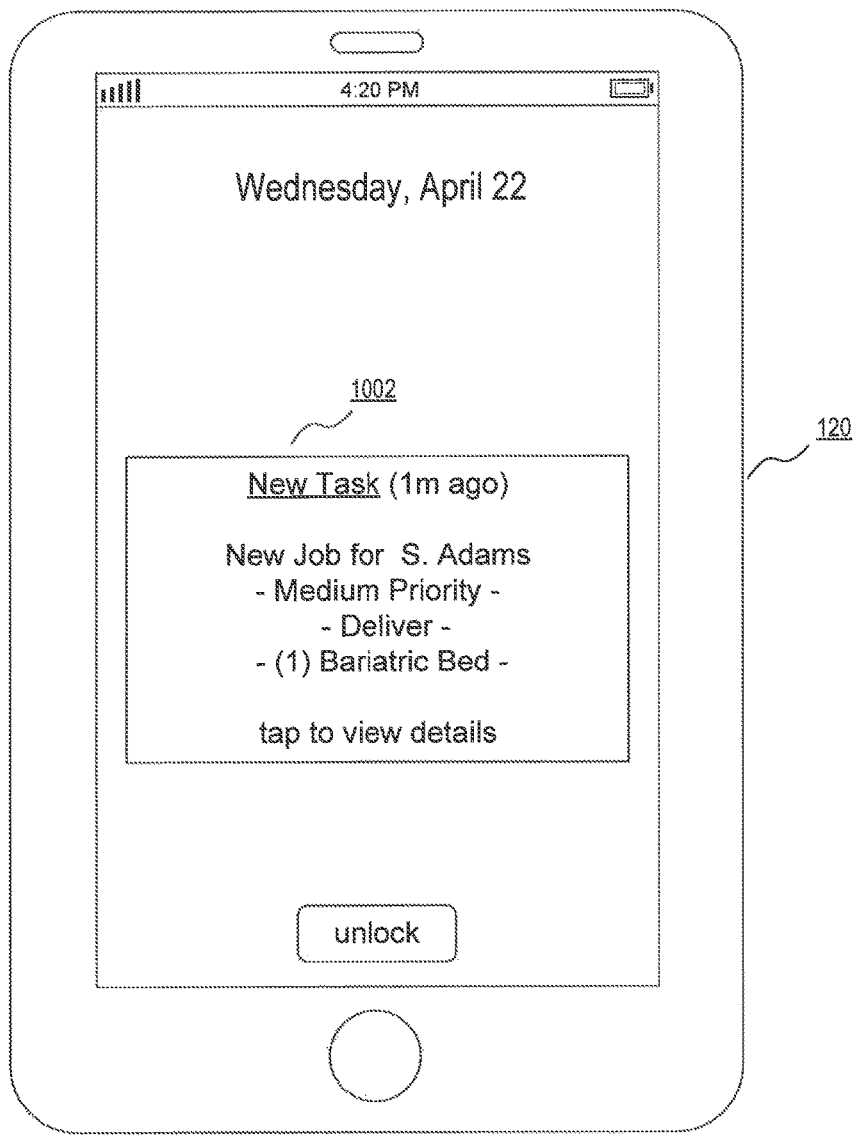
FIGS. 10 and 11 are illustrations of examples of task notification and management interfaces, consistent with embodiments of the present disclosure.

FIG. 10 is an illustration of an example of a task notification interface 1000. Display 310 of user device 120 may display interface 1000 in response to instructions from network server 160, to alert a responder that a new task is assigned to them. Interface 1000 may include a notification box 1002, to provide essential details of the task assignment. Notification box 1002 may include some or all of the attributes 802 included in the task assignment, depending on the settings of app 252 and the space available on display 310. In the example shown, notification box 102 may include, for example, a time that the new task was assigned, a priority level, a category of the task, and equipment and/or supplies associated with the task.

In some embodiments, network server 160 may transmit instructions for displaying notification box 1002 to user device 120 via any means of data transmission discussed above or known in the art. For example, network server 160 may transmit instructions for notification box 1002 via network 150 to local network 110 of facility system 102. Alternatively, network server 160 may transmit notification 1002 via a network other than network 150, such as a cellular or satellite communication system. In some embodiments, network server 160 may instruct third party server 170 to generate and transmit instructions for displaying notification box 1002. In such embodiments, third party server 170 may be operated by a notification service such as Apple notifications, Android notifications, or Blackberry notifications. In such embodiments, third party server 170 may receive instructions from network server 160, and then transmit instructions for displaying notification box 1002 to user device 120.

In some embodiments, network server 160 may transmit instructions for notification box 1002 via other communication means such as, for example, SMS message, a recorded audio message delivered via plain old telephone service (POTS), or to a provider of paging services.

Figure 11:
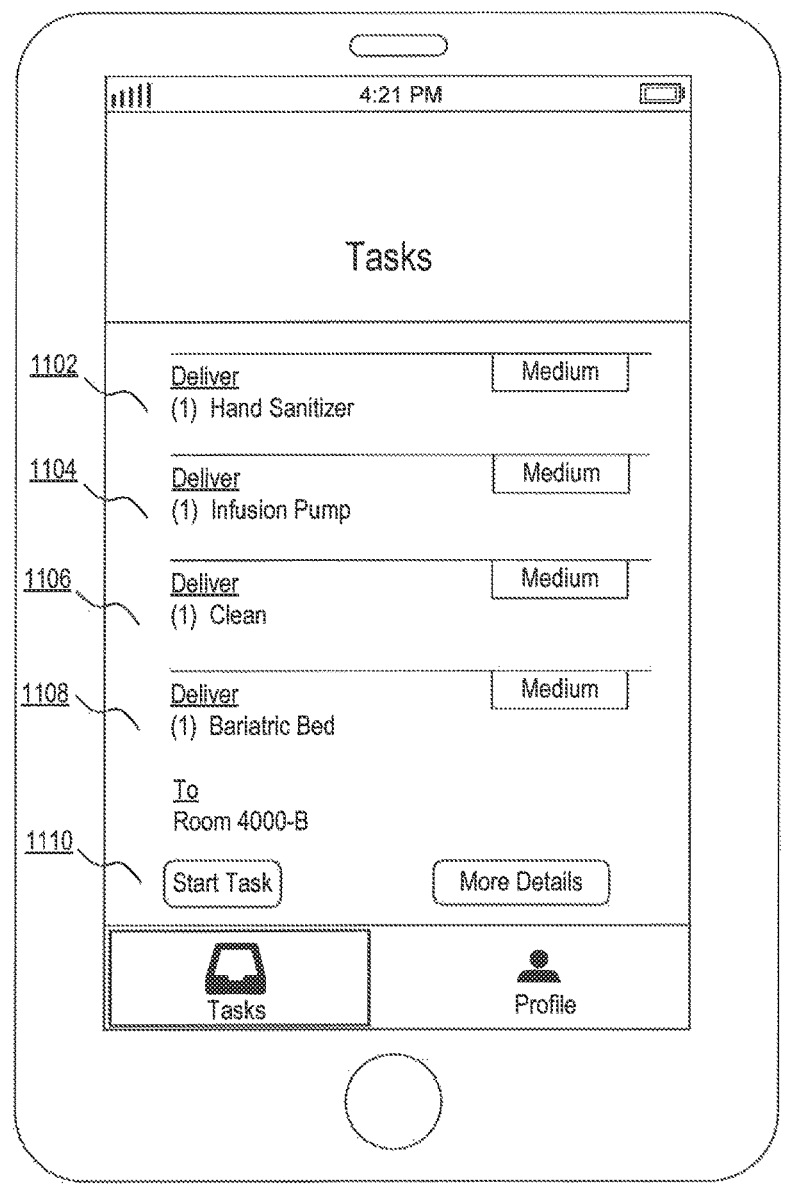

FIG. 11 is an illustration of a task management interface 1100. Display 310 of user device 120 may display interface 1100 in response to instructions received from network server 160. In some embodiments, app 252 may generate and display interface 1100 based on the received instructions. User 125 may enable mobile task management interface 1100 by interacting with notification box 1002 (in FIG. 10), or by navigating through one or more interfaces of app 252 to display assigned tasks.

In some embodiments, interface 1100 may display tasks assigned to an employee such as user 125, such as tasks 1102, 1104, 1106, and 1108. Tasks 1102, 1104, 1106, and 1108 may include some or all of the attributes 602 associated with each task.

In some embodiments, interface 1100 may include a button such as interface element 1110 which, when selected, notifies network server 160 that the employee has started working on the task. In response to selection of interface element 1110 by user 125, user device 120 may instruct network server 160 to update employee information (e.g. employee data 449 of network server 160) to reflect that user 125 has begun the task. Network server 160 may then update one or more database entries associated with the employee and the task. In some embodiments, network server 160 may generate and transmit one or more notifications to any interested parties such as, for example, the task requestor and/or dispatcher, indicating that the assigned employee is working on the task.

In some embodiments, app 252 may include one or more interfaces (not shown in figures) for entering information related to task progress, task completion, and/or delays. For example, while working on a task, an employee such as user 125 may select one or more interlace elements in an interface generated by app 252 to indicate that a step of the task is complete. Upon selection of the interface element, app 252 may cause user device 120 to inform network server 160 that a step of the task has been completed, and a timestamp of the step completion. In some embodiments, selection of one or more interface elements may inform network server 160 that one or more steps of the task cannot be completed in the estimated time frame and by the expected completion time. For example, if a supply room having necessary equipment is locked or blocked, or if a necessary piece of equipment is unexpectedly damaged, then the employee may indicate via app 252 that one or more steps cannot be completed on time. In some embodiments, selection on an interface element may indicate that the step must be delayed for an estimated time period, such as 30 minutes or an hour.

In some embodiments, selection of another interface element may indicate that the step must be suspended, i.e. delayed indefinitely. In response, network server 160 may unassign the task and queue the task for reevaluation and reassignment at a later time. For example, if an employee arrives at a storage room to find that the only available infusion pump is damaged beyond immediate repair, the employee may suspend the task. In some embodiments, the employee may manually indicate that the task should be suspended and reassigned at a later time. In other embodiments, network server 160 may automatically suspend the task, if the employee delays the task with a delay time that exceeds a predetermined threshold such as, for example, 3 hours. Network server 160 may unassign the task from the employee, and attempt to reassign the task after a predetermined time period. In some embodiments, network server 160 may also automatically generate a new task for repairing the infusion pump and/or an emergency request to transport an infusion pump from another facility. Network server 160 may determine an estimated time for transporting and/or repairing the infusion pump, and attempt to reassign the infusion pump delivery task upon completion of the transport/repair task, to the another employee identified using process 500. Thus, in some embodiments network server 160 may automatically identify the need for additional tasks based on occurrences or conditions that arise in current tasks. In such situations, network server 160 may automatically generate the additional tasks based on the detected occurrences and/or conditions, and automatically assign the additional tasks to the proper employees using process 500.

Network server 160 may also automatically create additional tasks at the time of task creation and/or assignment via process 500. For example, if at step 502, network server 160 receives task information for a task that requires an item, network server 160 may determine whether the item is available or present at an expected location. If the item is not present or is otherwise unavailable, network server 160 may create a new task for delivering the item. As noted above, network server 160 may delay, unassign, or reassign the task requiring the item, based on the timing involved in delivering the item.

In some embodiments, network server 160 may automatically generate and assign tasks according to a predetermined schedule, or in response to one or more trigger conditions. As a first example, network server 160 may receive, from a requestor, or dispatcher, a schedule for restocking a medicine storage room every 7 days. Network server may automatically assign the recurring task according to the schedule, to the correct employee for the task given current workload conditions and employee availabilities. In some embodiments, the medicine storage room may include one or more inventory level sensors, to detect an inventory of medicine containers and/or doses remaining in storage. Network server 160 may determine if the inventory level drops below a predetermined threshold, and create and assign one or more tasks based on the detected inventory level. In some embodiments, sensor devices disposed throughout the facility may include necessary processing capabilities and logic to compare sensed conditions (such as an inventory level) to one or more predetermined thresholds, and transmit a task request to network server 160 upon detecting that a predetermined threshold is exceeded.

As a second example, network server 160 may monitor one or more trigger conditions, such as a temperature sensor in a cold medicine storage room. If the detected temperature exceeds a predetermined threshold, network server 160 may automatically generate a high priority task to investigate the failed temperature control. Network server 160 may execute process 500 to determine which employees are currently available with the proper skill set to investigate and/or repair the cold storage room, determine which employees have a low workload to address the high priority task, and which employees are closest to the cold storage room and/or a room with the necessary diagnostic and repair tools. After considering these and other necessary factors, network server 160 may identify one or more employees suitable and available for the task, and generate instructions for providing a notification box 1002 for the task on the selected employee's user device 120. In some embodiments, network server 160 may update one or more database entries to identify the selected employee as assigned to the task.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A computerized system for generating data to display a task notification on a selected device for a service task performed in a medical facility, the system comprising:
   one or more sensor devices located in the medical facility, wherein the sensors comprise one or more of an inventory level sensor, an occupancy sensor, a temperature sensor, a humidity sensor, a proximity sensor, a door access sensor, or a room access sensor;
   at least one processor; and
   a storage medium comprising instructions that, when executed by the at least one processor, cause the at least one processor to perform operations comprising:
   detecting that sensor data from the sensor devices exceeded or fell below a threshold;
   receiving, at the at least one processor from a network, task information for a task that is pending assignment in a facility system, the task information including a requested task start time, at least one task location, and one or more required skills, the task information being received in response to detecting that the sensor data from the sensor devices exceeded or fell below the threshold;

receiving, from a networked database, employee information associated with a plurality of employees, the employee information including:

employee skills previously entered in the database by an authority figure associated with the plurality of employees or automatically identified based on previously-completed tasks, and workload information associated with uncompleted tasks assigned to the plurality of employees;

receiving, from devices associated with the plurality of employees, real-time location data of the plurality of employees, wherein the real-time location data is determined based on detection, by a receiver in the facility system, of an electronic tag associated with each one of the plurality of employees and indicates an employee's location within the facility system;

determining the task is not available for automatic assignment by determining that the task is associated with safety considerations or task categories not integrated in the automatic assignment rule set;

determining the task is eligible for automatic assignment by determining that the task information includes factors that are integrated within an automatic assignment rule set;

responsive to determining that the task is eligible for automatic assignment:

applying the automatic assignment rule set to determine a score for each one of the plurality of employees, the score being proportionate to a number of matches between the task location and based on each employee's real-time location within the facility system and between the one or more required skills and the employee skills, and assigning the task to an automatically selected employee, the automatically selected employee having a highest score of the determined scores;

responsive to determining that the task is not available for automatic assignment:

generating data to display, in a client device associated with the authority figure, a first graphical user interface comprising:

a plurality of data fields allowing entry of information, at least one of the plurality of data fields being automatically populated based on entries in other data fields, an employee list ranking, the employee list ranking sorting the plurality of employees based on the score, the plurality of employees being associated with a plurality of first buttons, and a second button, and receiving, from the client device, a manually selected employee from the employee list ranking by a user selecting the second button and at least one of the plurality of first buttons;

assigning the task to the manually selected employee from the employee list ranking in response to the user selecting the second button and the at least one plurality of first buttons;

generating data to display a second graphical user interface in the selected device, the second graphical user interface comprising a notification box displaying chosen attributes of the task, the chosen task attributes including a subset of task attributes of the task or all task attributes of the task based on the space available on a display of the selected device;

receiving a user interaction with the notification box;

generating data to display a third graphical user interface in the selected device in response to receiving the user interaction with the notification box, the third graphical user interface comprising a plurality of tasks assigned to the selected employee and a start notification button; and creating at least one database entry associated with the assigned task.

2. The computerized system of claim 1, further comprising:

receiving one or more updates from the automatically or manually selected employee indicating progress toward completion of the assigned task; and updating the database entry based on the one or more received updates.

3. The computerized system of claim 1, further comprising:

determining that a predetermined time period for completing the assigned task is exceeded; and automatically transmitting a notification to at least one of the automatically or manually selected employee or a requester of the assigned task.

4. The computerized system of claim 1, further comprising:

identifying, based on one or more stored rules, an equipment or supply item associated with the assigned task; and determining a location associated with the identified equipment or supply item, wherein the at least one processor determines matches based in part on a proximity between each employee's location within the facility system and the identified equipment or supply item.

5. The computerized system of claim 1, further comprising:

receiving an indication associated with a delay in completing the assigned task;

determining a delay period associated with the indication;

determining whether the delay period exceeds a predetermined threshold; and when the delay period exceeds the predetermined threshold, automatically unassigning the assigned task.

6. The computerized system of claim 1, wherein the at least one processor is further configured to:

determine that the real-time location data indicates a delay in completing the current task;

unassign the first task from the automatically or manually selected employee; and assign the task to a second selected employee, the second selected employee being the employee from the plurality of employees with a second highest score or a second employee received from the client device.

7. The computerized system of claim 1, wherein the plurality of data fields comprise a field for entry of a location associated with the task and a field for entry of a priority associated with the task.

8. The computerized system of claim 1, wherein the employee list ranking change dynamically in response to entries in the plurality of data fields to display only employees which meet a criteria identified based on the entries in the plurality of data fields.

9. The computerized system of claim 1, wherein generating data to display a second graphical user interface comprises transmitting instructions to a third party server for displaying the second graphical user interface, the third party server being operated by a notification service.

10. The computerized system of claim 7, wherein the user interaction with the notification box comprises tapping the notification box.

11. The computerized system of claim 10, wherein the notification box displays a time when the new task was assigned, the priority associated with the task, a category of the task, and equipment associated with the task.

12. A computerized method for generating data to display a task notification on a selected device for a service task performed in a medical facility, the system comprising:
  detecting that sensor data from one or more sensor devices located in the medical facility exceeded or fell below a threshold, wherein the sensors comprise one or more of an inventory level sensor, an occupancy sensor, a temperature sensor, a humidity sensor, a proximity sensor, a door access sensor, or a room access sensor;
  receiving, by at least one processor from a network, task information for a task that is pending assignment in a facility system, the task information including a requested task start time, at least one task location, and one or more required skills, the task information being received in response to detecting that the sensor data from the sensor devices exceeded or fell below the threshold;
  receiving, from a networked database, employee information associated with a plurality of employees, the employee information including:
    employee skills previously entered in the database by an authority figure associated with the plurality of employees or automatically identified based on previously-completed tasks, and
    workload information associated with uncompleted tasks assigned to the plurality of employees;
  receiving, from devices associated with the plurality of employees, real-time location data of the plurality of employees, wherein the real-time location data is determined based on detection, by a receiver in the facility system, of an electronic tag associated with each one of the plurality of employees and indicates an employee's location within the facility system;
  determining the task is not available for automatic assignment by determining that the task is associated with safety considerations or task categories not integrated in the automatic assignment rule set;
  determining the task is eligible for automatic assignment by determining that the task information includes factors that are integrated within an automatic assignment rule set;
  responsive to determining that the task is eligible for automatic assignment:
    applying the automatic assignment rule set to determine a score for each one of the plurality of employees, the score being proportionate to a number of matches between the task location and based on each employee's real-time location within the facility system, and between the one or more required skills and the employee skills, and
    assigning the task to an automatically selected employee, the automatically selected employee having a highest score of the determined scores;
  responsive to determining that the task is not available for automatic assignment:
    generating data to display, in a client device associated with the authority figure, a first graphical user interface comprising:
      a plurality of data fields allowing entry of information, at least one of the plurality of data fields being automatically populated based on entries in other data fields,
      an employee list ranking, the employee list ranking sorting the plurality of employees based on the score, the plurality of employees being associated with a plurality of first buttons, and
      a second button; and
    receiving, from the client device, a manually selected employee from the employee list ranking by a user selecting the second button and at least one of the plurality of first buttons;
    assigning the task to the manually selected employee from the employee list ranking in response to the user selecting the second button and the at least one of the plurality of first buttons;
  generating data to display a second graphical user interface in the selected device, the second graphical user interface comprising a notification box displaying chosen task attributes of the task, the chosen task attributes including a subset of task attributes of the task or all task attributes of the task based on the space available on a display of the selected device;
  receiving a user interaction with the notification box;
  generating data to display a third graphical user interface in the selected device in response to receiving the user interaction with the notification box, the third graphical user interface comprising a plurality of tasks assigned to the selected employee and a start notification button; and
  creating at least one database entry associated with the assigned task.

13. The computerized method of claim 12, further comprising:
  receiving one or more updates from the automatically or manually selected employee indicating progress toward completion of the assigned task; and
  updating the database entry based on the one or more received updates.

14. The computerized method of claim 12, further comprising:
  determining that a predetermined time period for completing the assigned task is exceeded; and
  automatically transmitting a notification to at least one of the automatically or manually selected employee or a requester of the assigned task.

15. The computerized method of claim 12, further comprising:
  identifying, based on one or more stored rules, an equipment or supply item associated with the assigned task; and
  determining a location associated with the identified equipment or supply item, wherein the at least one processor determines matches based in part on a proximity between each employee's location within the facility system and the identified equipment or supply item.

16. The computerized method of claim 12, further comprising:
  receiving an indication associated with a delay in completing the assigned task;
  determining a delay period associated with the indication;
  determining whether the delay period exceeds a predetermined threshold; and
  when the delay period exceeds the predetermined threshold, automatically unassigning the assigned task.

17. A non-transitory computer-readable medium storing instructions which, when executed, cause one or more processors to perform operations for generating data to display a task notification on a selected device for a service task performed in a medical facility, the operations comprising:
- detecting that sensor data from one or more sensor devices located in the medical facility exceeded or fell below a threshold, wherein the sensors comprise one or more of an inventory level sensor, an occupancy sensor, a temperature sensor, a humidity sensor, a proximity sensor, a door access sensor, or a room access sensor;
- receiving, at the at least one processor from a network, task information for a first task that is pending assignment, the task information including a requested task start time, at least one task location, and one or more required skills, the task information being received in response to detecting that the sensor data from the sensor devices exceeded or fell below the threshold;
- receiving, from a networked database, employee information associated with a plurality of employees, the employee information including:
  - employee skills previously entered in the database by an authority figure associated with the plurality of employees or automatically identified based on previously-completed tasks, and
  - workload information associated with uncompleted tasks assigned to the plurality of employees;
- receiving, from devices associated with the plurality of employees, real-time location data of the plurality of employees, wherein the real-time location data is determined based on detection, by a receiver in the facility system, of an electronic tag associated with each one of the plurality of employees and indicates an employee's location within the facility system;
- determining the task is not available for automatic assignment by determining that the task is associated with safety considerations or task categories not integrated in the automatic assignment rule set;
- determining the task is eligible for automatic assignment by determining that the task information includes factors that are integrated within an automatic assignment rule set;
- responsive to determining that the task is eligible for automatic assignment:
  - applying the automatic assignment rule set to determine a score for each one of the plurality of employees, the score being proportionate to a number of matches between the task location and based on each employee's real-time location within the facility system, and between the one or more required skills and the employee skills, and
  - assigning the task to an automatically selected employee, the automatically selected employee having a highest score of the determined scores;
- responsive to determining that the task is not available for automatic assignment:
  - generating data to display, in a client device associated with the authority figure, a first graphical user interface comprising:
    - a plurality of data fields allowing entry of information, at least one of the plurality of data fields being automatically populated based on entries in other data fields,
    - an employee list ranking, the employee list ranking sorting the plurality of employees based on the score, the plurality of employees being associated with a plurality of first buttons, and
    - a second button; and
  - receiving, from the client device, a manually selected employee from the employee list ranking by a user selecting the second button and at least one of the plurality of first buttons;
  - assigning the task to the manually selected employee from the employee list ranking in response to the user selecting the second button and the at least one of the plurality of first buttons;
- generating data to display a second graphical user interface in the selected device, the second graphical user interface comprising a notification box displaying chosen task attributes of the task, the chosen task attributes including a subset of task attributes of the task or all task attributes of the task based on the space available on a display of the selected device;
- receiving a user interaction with the notification box;
- generating data to display a third graphical user interface in the selected device in response a user interacting with the notification box, the third graphical user interface comprising a plurality of tasks assigned to the selected employee and a start notification button; and
- creating at least one database entry associated with the assigned task.

18. The computerized system of claim 17, further comprising:
- receiving one or more updates from the automatically or manually selected employee indicating progress toward completion of the assigned task; and
- updating the database entry based on the one or more received updates.

19. The computerized system of claim 17, further comprising:
- identifying, based on one or more stored rules, an equipment or supply item associated with the assigned task; and
- determining a location associated with the identified equipment or supply item, wherein the at least one processor determines matches based in part on a proximity between each employee's location within the facility system and the identified equipment or supply item.

20. The computerized system of claim 17, further comprising:
- receiving an indication associated with a delay in completing the assigned task;
- determining a delay period associated with the indication;
- determining whether the delay period exceeds a predetermined threshold; and
- when the delay period exceeds the predetermined threshold, automatically unassigning the assigned task.

* * * * *